US010220107B2

(12) United States Patent
Egawa et al.

(10) Patent No.: US 10,220,107 B2
(45) Date of Patent: Mar. 5, 2019

(54) PLASMA GENERATING METHOD INCLUDING GENERATING FIRST PLASMA WITHOUT SUPPLYING FIRST GAS IN LIQUID AND GENERATING SECOND PLASMA IN FIRST GAS, AND PLASMA GENERATING APPARATUS

(71) Applicant: Panasonic Intellectual Property Management Co., Ltd., Osaka (JP)

(72) Inventors: Minoru Egawa, Osaka (JP); Yoshihiro Sakaguchi, Hyogo (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 73 days.

(21) Appl. No.: 15/464,877

(22) Filed: Mar. 21, 2017

(65) Prior Publication Data

US 2017/0281813 A1   Oct. 5, 2017

(30) Foreign Application Priority Data

Mar. 31, 2016   (JP) ................. 2016-072360

(51) Int. Cl.
*A61L 2/14* (2006.01)
*H01J 37/32* (2006.01)
(Continued)

(52) U.S. Cl.
CPC .............. *A61L 2/14* (2013.01); *C02F 1/4608* (2013.01); *H01J 37/3244* (2013.01); *H01J 37/32935* (2013.01); *A61L 2202/11* (2013.01); *A61L 2202/14* (2013.01); *C02F 1/4672* (2013.01); *C02F 2101/30* (2013.01);
(Continued)

(58) Field of Classification Search
CPC .... A61L 2/14; A61L 2202/11; A61L 2202/14; C02F 1/4608; C02F 1/4672; C02F 2101/30; C02F 2209/006; C02F 2303/04; C02F 2305/023; H01J 37/3244; H01J 37/32935
See application file for complete search history.

(56) References Cited

U.S. PATENT DOCUMENTS

| 2009/0098062 | A1 | 4/2009 | Bobbert |
| 2013/0333841 | A1 | 12/2013 | Narita et al. |
| 2014/0054242 | A1* | 2/2014 | Imai ..................... C02F 1/4608 210/748.17 |

FOREIGN PATENT DOCUMENTS

| JP | 2005-058886 | 3/2005 |
| JP | 2007-207540 | 8/2007 |

(Continued)

*Primary Examiner* — Timothy C Cleveland
(74) *Attorney, Agent, or Firm* — McDermott Will & Emery LLP

(57) ABSTRACT

A plasma generating method, used in a plasma generating apparatus which includes a container, a first electrode, and a second electrode, includes: supplying a liquid in the container so that the second electrode is in contact with the liquid; in a first period, generating first plasma in a bubble generated in the liquid by applying a first voltage between the first electrode and the second electrode; supplying a first gas in the liquid in a second period after the first period; and generating second plasma in the first gas by applying a second voltage between the first electrode and the second electrode. In generating the first plasma, the first gas is not supplied in the liquid. The bubble contains a second gas.

7 Claims, 9 Drawing Sheets

(51) Int. Cl.
*C02F 1/46* (2006.01)
*C02F 1/467* (2006.01)
*C02F 101/30* (2006.01)

(52) U.S. Cl.
CPC .... *C02F 2209/006* (2013.01); *C02F 2303/04* (2013.01); *C02F 2305/023* (2013.01)

(56) References Cited

FOREIGN PATENT DOCUMENTS

| | | |
|---|---|---|
| JP | 2009-513605 | 4/2009 |
| JP | 2012-204248 | 10/2012 |
| JP | 2014-113517 | 6/2014 |

\* cited by examiner

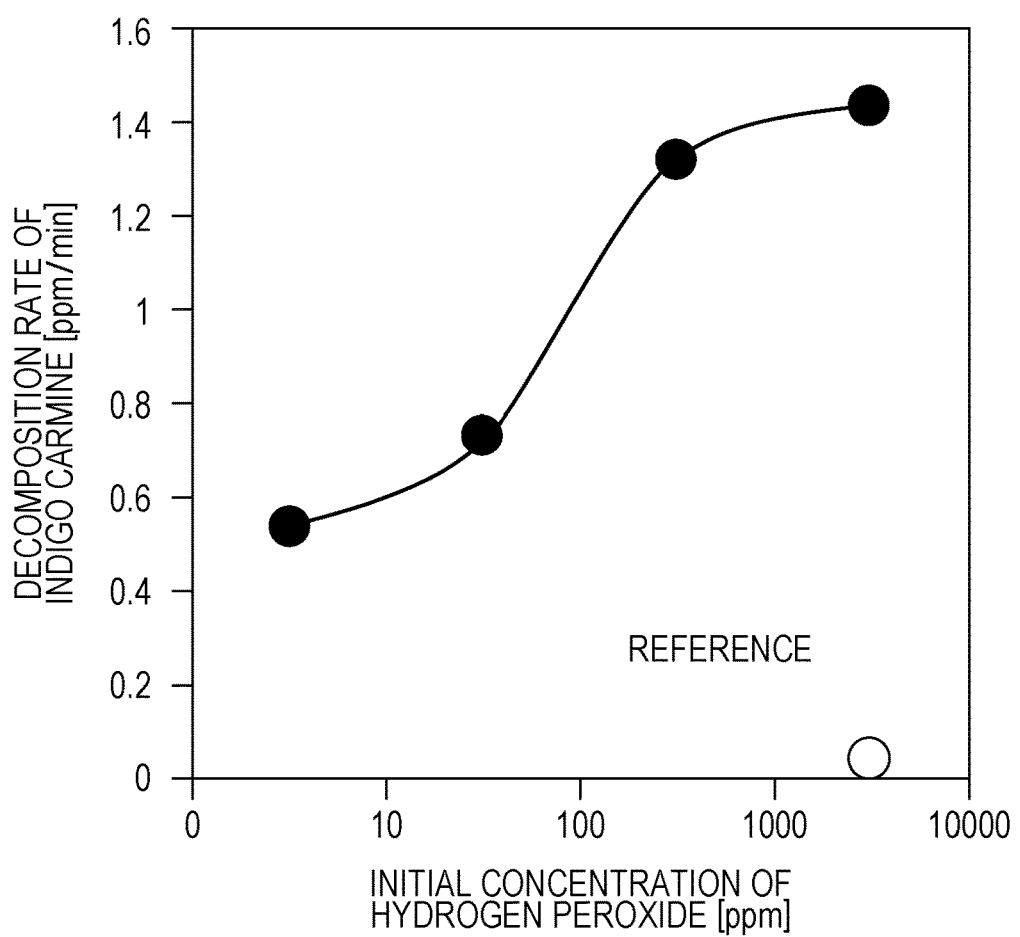

PLASMA GENERATING METHOD INCLUDING GENERATING FIRST PLASMA WITHOUT SUPPLYING FIRST GAS IN LIQUID AND GENERATING SECOND PLASMA IN FIRST GAS, AND PLASMA GENERATING APPARATUS

BACKGROUND

1. Technical Field

The present disclosure relates to a plasma generating method and a plasma generating apparatus.

2. Description of the Related Art

Heretofore, a technique using plasma for purification and sterilization of liquid or gas has been researched. For example, Japanese Unexamined Patent Application Publication No. 2005-058886 has disclosed a plasma generating apparatus in which microorganisms and bacteria are sterilized by active species generated by plasma.

In the plasma generating apparatus disclosed in Japanese Unexamined Patent Application Publication No. 2005-058886, treatment baths, each of which performs a high voltage pulse treatment on wastewater, are disposed and connected in a multistage in-line manner. In a front-stage treatment bath, a generation reaction of oxidizing radicals is mainly performed by a high voltage pulse discharge. In a rear-stage treatment bath, oxidation decomposition of organic products is performed using hydrogen peroxide generated by the above oxidizing radicals and oxidizing radicals generated by a high voltage pulse discharge performed in the presence of the above hydrogen peroxide.

SUMMARY

In one general aspect, the techniques disclosed here feature a plasma generating method, used in a plasma generating apparatus which includes a container, a first electrode, and a second electrode, the method comprising: supplying a liquid in the container so that the second electrode is in contact with the liquid; in a first period, generating first plasma in a bubble generated in the liquid by applying a first voltage between the first electrode and the second electrode; supplying a first gas in the liquid in a second period after the first period; and generating second plasma in the first gas by applying a second voltage between the first electrode and the second electrode. In generating the first plasma, the first gas is not supplied in the liquid. The bubble contains a second gas.

It should be noted that general or specific embodiments may be implemented as a system, a method, an integrated circuit, a computer program, a storage medium, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 8 is a graph showing a measurement result of a decomposition rate of indigo carmine with respect to an initial concentration of hydrogen peroxide of the plasma generating apparatus according to the embodiment.

DETAILED DESCRIPTION

Figure 1:
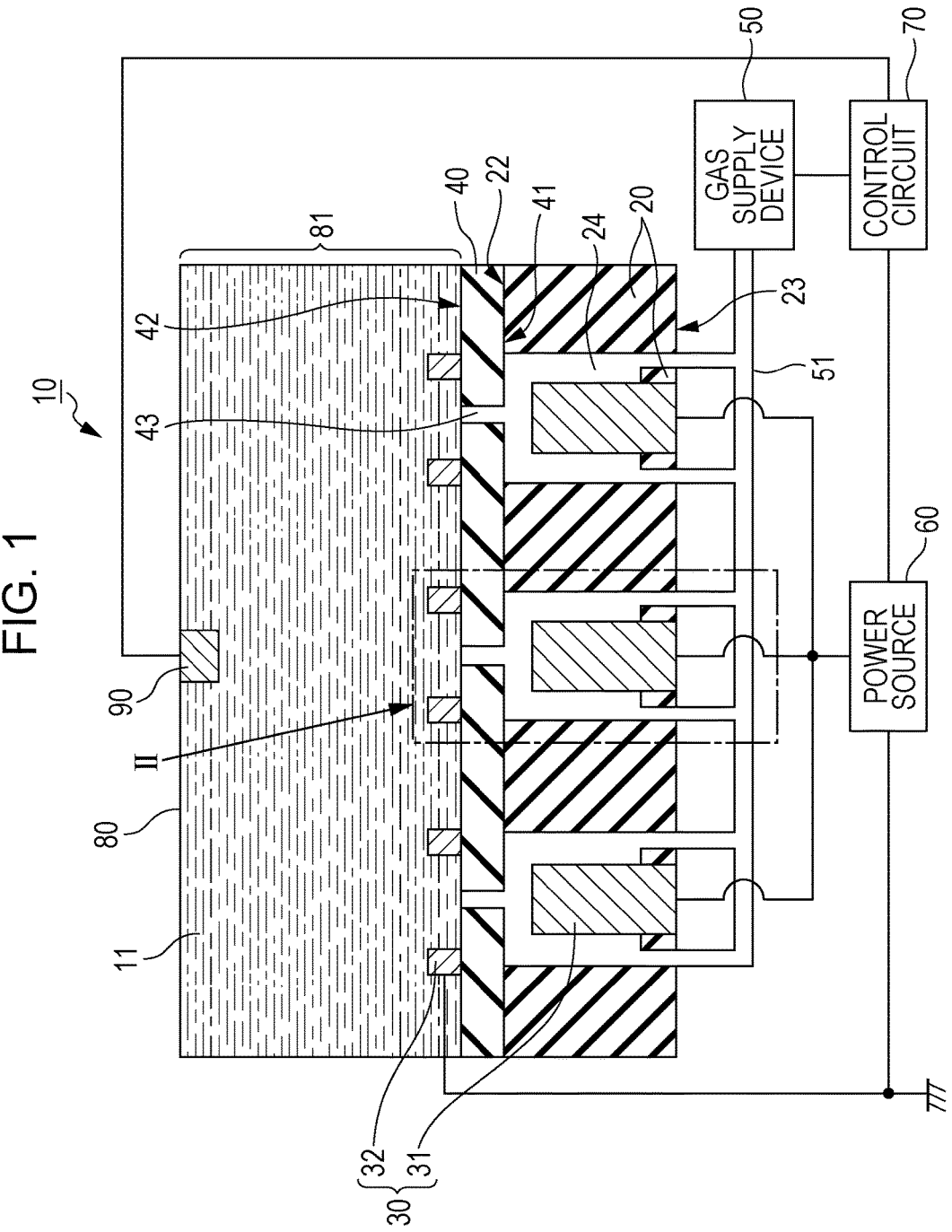
FIG. 1 is a schematic view showing the structure of a plasma generating apparatus according to an embodiment.

In the plasma generating apparatus described above, since a plurality of treatment baths including the front-stage treatment bath and the rear-stage treatment bath are provided, the size of a treatment device is increased.

On the other hand, by a plasma generating apparatus according to one aspect of the present disclosure, a liquid having a high oxidizing power can be efficiently generated using only one treatment bath.

Overview of the Present Disclosure

A plasma generating method according to a first aspect of the present disclosure, used in a plasma generating apparatus which includes a container, a first electrode, and a second electrode, comprises: supplying a liquid in the container so that the second electrode is in contact with the liquid; in a first period, generating first plasma in a bubble generated in the liquid by applying a first voltage between the first electrode and the second electrode; supplying a first gas in the liquid in a second period after the first period; and generating second plasma in the first gas by applying a second voltage between the first electrode and the second electrode. In generating the first plasma, the first gas is not supplied in the liquid. The bubble contains a second gas.

In the plasma generating method according to the first aspect of the present disclosure, hydrogen peroxide may be generated in the liquid by the first plasma. The method may further comprise: determining whether or not a concentration of the hydrogen peroxide in the liquid is a predetermined value or more, and in the second period, when the concentration is determined to be the predetermined value or more, the supplying the first gas is performed.

In the first aspect, the predetermined value is for example, 10 ppm.

The plasma generating method according to the first aspect of the present disclosure may further comprise, after the first period and before the second period, stopping an application of the first voltage between the first electrode and the second electrode.

In the plasma generating method according to the first aspect of the present disclosure, hydrogen peroxide may be generated in the liquid by the first plasma. The method may further comprise after the stopping the application of the first voltage is performed, determining whether or not a concentration of the hydrogen peroxide in the liquid is lower than a predetermined value; and when the concentration is determined to be lower than the predetermined value, again generating the first plasma. The gas may be at least one selected from the group consisting of air, nitrogen, and oxygen. In generating the first plasma, no gas may be supplied in the liquid.

A plasma generating apparatus according to a second aspect of the present disclosure comprises: a container for holding a liquid; a first electrode; a second electrode disposed at a position in contact with the liquid when the liquid is held in the container; a power source that, in operation, applies a voltage between the first electrode and the second electrode; a gas supply device that, in operation, supplies a first gas in the liquid; and a control circuit that, in operation, controls operations of the power source and the gas supply device, in which the control circuit causes: (I) in a first period, the gas supply device not to supply the first gas in the liquid and the power source to apply a first voltage between the first electrode and the second electrode so as to generate first plasma in a bubble containing a second gas generated by evaporation of the liquid, and (II) in a second period after the first period, the gas supply device to supply the first gas in the liquid and the power source to apply a second voltage between the first electrode and the second electrode so as to generate second plasma in the first gas.

Accordingly, by a simple control in which the supply of the first gas from the gas supply device is performed or not, a liquid having a high oxidizing power can be efficiently generated. In particular, by performing discharge without supplying the first gas from the gas supply device in the first period, hydrogen peroxide can be efficiently stored in the liquid. In addition, in the second period after the first period, by performing discharge while the first gas is supplied from the gas supply device, oxidizing radicals containing OH radicals can be efficiently generated using the above hydrogen peroxide. That is, a liquid having a high oxidizing power can be generated. Hence, since sterilization of the liquid or decomposition of organic substances can be efficiently performed, the plasma generating apparatus is able to have a high water treatment performance. In addition, since the storage of hydrogen peroxide and the generation of a highly oxidizing liquid containing OH radicals can be performed by only one treatment bath, the size of the plasma generating apparatus can be reduced.

In the plasma generating apparatus according to the second aspect of the present disclosure, one of outer walls of the container may include a through-hole, in the first period, the liquid may be brought into contact with the first electrode through the through-hole, and in the second period, the first gas may be supplied in the liquid through the through-hole. The one of the outer walls may be a bottom wall of the container.

In the plasma generating apparatus according to the second aspect of the present disclosure, the control circuit may, in operation, further determine whether or not a concentration of the hydrogen peroxide in the liquid is a predetermined value or more, and when the concentration is determined to be the predetermined value or more, the control circuit may cause the gas supply device to supply the first gas in the liquid and the power source to apply the second voltage between the first electrode and the second electrode.

Accordingly, when the concentration of hydrogen peroxide is the predetermined value or more, since the second plasma is generated, the sterilization of the liquid or the decomposition of organic substances can be performed at a high rate. Hence, the plasma generating apparatus described above is able to have a high water treatment performance. In addition, for example, when the concentration of organic substances in the liquid is high, the predetermined value of the concentration of hydrogen peroxide is set high, and when the concentration of hydrogen peroxide is the predetermined value or more, the second plasma is generated. Accordingly, even when the concentration of organic substances in the liquid is high, the decomposition rate can be increased. That is, in accordance with the concentration of organic substances, the decomposition rate thereof can be adjusted.

In the case described above, the predetermined value is for example, 10 ppm.

In addition, the plasma generating apparatus according to the second aspect of the present disclosure may further comprise a hydrogen peroxide sensor that, in operation, measures the concentration of the hydrogen peroxide in the liquid, and the control circuit may determine whether or not the concentration is the predetermined value or more using the hydrogen peroxide sensor.

Accordingly, since the concentration of hydrogen peroxide in the liquid can be measured, the control of the concentration of hydrogen peroxide can be easily performed. For example, the concentration of hydrogen peroxide at which the generation of the first plasma is finished and/or the concentration of hydrogen peroxide at which the generation of the second plasma is started can be precisely set.

In addition, the plasma generating apparatus according to the second aspect of the present disclosure may include a plurality of first electrodes and a plurality of second electrodes.

Accordingly, in one treatment bath, discharge occurs at a plurality of electrode pairs each including the first electrode and the second electrode, and a space in which plasma is generated can be increased. Hence, the rate of storage of hydrogen peroxide and the rate of sterilization or the rate of decomposition of organic substances using the above hydrogen peroxide can be improved.

In addition, in the plasma generating apparatus according to the second aspect of the present disclosure, after the first period and before the second period, the control circuit may further cause the power source to stop an application of the first voltage between the first electrode and the second electrode.

Accordingly, in the case in which although the generation of the first plasma is finished, it is not a timing to start the generation of the second plasma, hydrogen peroxide generated in the first period can be stored in the liquid. Hydrogen peroxide has a weak oxidizing power as compared to that of oxidizing radicals containing OH radicals and is stabler than that. Hence, hydrogen peroxide can be stored in the liquid for a certain period of time. Accordingly, even at the timing at which the second plasma is to be generated, since hydrogen peroxide is stored in the liquid, oxidizing radicals containing OH radicals can be efficiently generated. That is, a liquid having a high oxidizing power can be efficiently generated. Hence, since the sterilization of the liquid or the decomposition of organic substances can be efficiently performed, the plasma generating apparatus described above is able to have a high water treatment performance. In addition, since the discharge can be stopped until the timing at which the second plasma is generated, the electric power can be reduced. In this case, the timing at which the second plasma is generated indicates, for example, a timing at which the sterilization of the liquid itself or the decomposition of organic substances is started. Alternatively, the timing described above indicates a timing at which by using a liquid containing oxidizing radicals, the sterilization of another liquid or gas or the decomposition of organic substances is started.

In addition, in the plasma generating apparatus according to the second aspect of the present disclosure, after the application of the first voltage between the first electrode and the second electrode by the power source is stopped, the control circuit may further determine whether or not a concentration of the hydrogen peroxide in the liquid is lower than a predetermined value, and when the concentration is determined to be lower than the predetermined value, the control circuit may cause the gas supply device not to supply the first gas in the liquid and the power source to again apply the first voltage between the first electrode and the second electrode.

Accordingly, even when the concentration of hydrogen peroxide is decreased when the discharge is stopped, since the generation of the first plasma is again started, the concentration of hydrogen peroxide can be maintained at a predetermined value or more. At the timing at which the second plasma is generated, since hydrogen peroxide having a concentration of a predetermined value or more is contained in the liquid, the sterilization of the liquid or the decomposition of organic substances can be performed at a high rate. Hence, the plasma generating apparatus described above is able to have a high water treatment performance.

In addition, in the plasma generating apparatus according to the second aspect of the present disclosure, the first voltage may be the same as the second voltage.

Accordingly, in both of the generation of the first plasma and the generation of the second plasma, by the use of only one power source, the voltage can be applied between the first electrode and the second electrode. That is, the number of power sources can be reduced. Hence, the cost of the plasma generating apparatus can be reduced.

In the present disclosure, all or some of circuits, units, devices, members, or portions or all or some of functional blocks of a block diagram may be implemented by at least one electronic circuit including a semiconductor device, a semiconductor integrated circuit (IC), or a large scale integrated circuit (LSI). LSI or IC may be integrated in one chip or may be formed in combination of a plurality of chips. For example, functional blocks other than a memory element may be integrated in one chip. In this case, although the semiconductor integrated circuit is called an LSI or an IC, the name of the integrated circuit is changed depending on the degree of integration, and for example, the integrated circuit may be called a system LSI, a very large scale integrated circuit (VLSI), or an ultra large scale integrated circuit (ULSI) in some cases. For the same purpose as described above, there may also be used a field programmable gate array (FPGA) in which programming is performed after an LSI is manufactured or a reconfigurable logic device in which reconfiguration of the connection or setup of circuit cells in an LSI can be performed.

Furthermore, all or some of functions or operations of the circuits, the units, the devices, the members, or the portions may be carried out by a software processing. In this case, the software is recorded in at least one non-transitory recording medium, such as a ROM, an optical disc, or a hard disc, and when the software is implemented by a processor, the function specified by the software is carried out by the processor and peripheral devices thereof. A system or an apparatus may include at least one non-transitory recording medium in which the software is recorded, the processor, and a required hardware device, such as an interface.

Hereinafter, embodiments will be described in detail with reference to the drawings.

In addition, the following embodiments all show comprehensive or concrete examples. The numerical values, the shapes, the materials, the constituent elements, the arrangement and connection thereof, the steps, the order of the steps, and the like shown in the following embodiments are described by way of example, and the present disclosure is not limited to those described above. In addition, among the constituent elements of the following embodiments, the constituent element which is not described in the independent claim representing the most generic concept will be described as an arbitrary constituent element.

Embodiments

Hereinafter, with reference to FIGS. 1 to 8, embodiments will be described.

[1-1. Structure]

Figure 2:
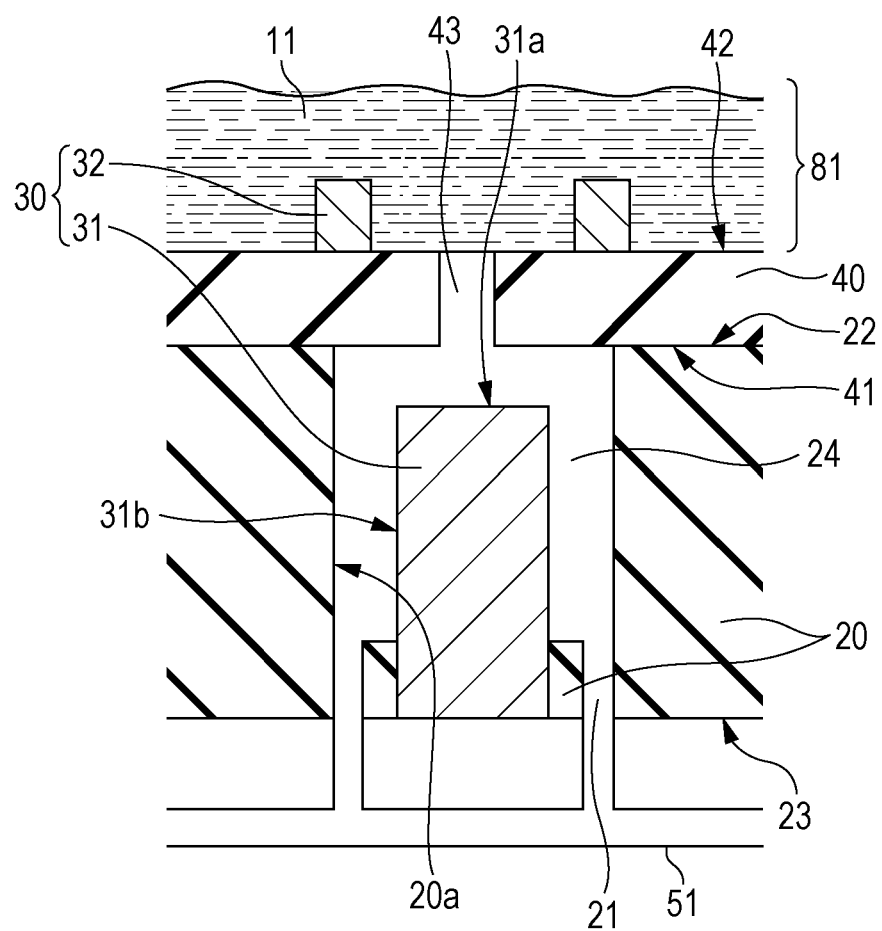
FIG. 2 is an enlarged schematic view showing the structure of the vicinity of an electrode of the plasma generating apparatus according to the embodiment.

First, the structure of a plasma generating apparatus according to one embodiment will be described with reference to FIGS. 1 to 3. FIG. 1 is a schematic view showing the structure of a plasma generating apparatus 10 according to this embodiment. FIG. 2 is an enlarged view (cross-sectional view) showing the structure of the vicinity of an electrode (region II shown by a chain line of FIG. 1) of the plasma generating apparatus 10 according to this embodiment.

The plasma generating apparatus 10 according to this embodiment comprises a plurality of first electrodes 31 disposed in an array form and generates plasma in the vicinity of each of the first electrodes 31. That is, the plasma generating apparatus 10 is a multipoint discharge-type plasma generating apparatus in which plasma generating sources are disposed in an array form.

As shown in FIGS. 1 and 2, the plasma generating apparatus 10 comprises an electrode support plate 20, a plurality of electrode pairs 30 including the plurality of first electrodes 31 and a plurality of second electrodes 32, an insulating plate 40, a gas supply device 50, a power source 60, a control circuit 70, and a hydrogen peroxide sensor 90. In addition, the plasma generating apparatus 10 also comprises a liquid holding portion 80 having a space 81 for holding a liquid 11. In particular, the space 81 in which the liquid 11 is received is present at a side opposite to the electrode support plate 20 and the plurality of first electrodes 31 with the insulating plate 40 interposed therebetween.

In this case, the liquid 11 is for example, water, such as purified water, tap water, or wastewater. In the plasma generating apparatus 10, without supplying a first gas 12, hydrogen peroxide is stored by generating a plasma 14 in the liquid 11, and while the first gas 12 is supplied, by generating the plasma 14 in a liquid 11 containing hydrogen peroxide, oxidizing radicals containing OH radicals are generated.

Accordingly, sterilization of the liquid 11 itself or decomposition of organic substances can be performed. Alternatively, by the use of the liquid 11 containing oxidizing radicals (that is, the plasma-treated liquid 11), sterilization of another liquid or gas can be performed. In addition, the plasma-treated liquid 11 can be used not only for sterilization but also for various other purposes.

Hereinafter, constituent elements forming the plasma generating apparatus 10 according to this embodiment will be described in detail with reference to FIGS. 1 to 3.

[1-1-1. Electrode Support Plate]

The electrode support plate 20 is one example of an insulating electrode support body supporting the first electrodes 31. In particular, the electrode support plate 20 is a plate-shaped member having a plurality of holes 25 arranged in an array form. In this embodiment, the electrode support plate 20 is formed of a heat-resistant resin material or a ceramic. For example, as the electrode support plate 20, a material formed of an epoxy resin impregnated in glass fibers or an alumina ceramic may be used.

The electrode support plate 20 is for example, a flat plate having an approximately rectangular shape. In addition, the shape of the electrode support plate 20 is not limited to that described above, and for example, a round plate or an oval plate may also be used. In addition, the electrode support plate 20 is not limited to a flat plate and may be a curved plate.

When the electrode support plate 20 is viewed in plan, the plurality of holes 25 are arranged in a two-dimensional manner. In this embodiment, for example, the plurality of holes 25 are regularly arranged both in the row direction and the line direction. In addition, the arrangement of the plurality of holes 25 is not limited to that described above and may be, for example, any one of a honeycomb, a one-dimensional, and a random form.

Figure 3:
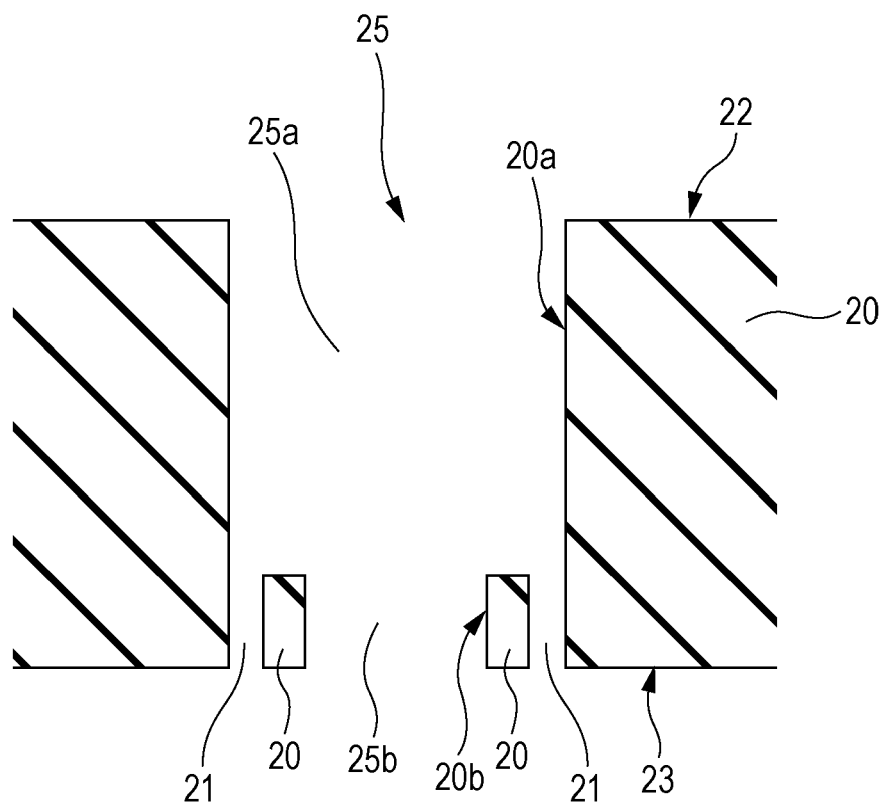
FIG. 3 is a cross-sectional view of an electrode support plate of the plasma generating apparatus according to the embodiment.

FIG. 3 is a cross-sectional view of the electrode support plate 20. For example, the holes 25 each have a cylindrical shape. The holes 25 are each formed of two through-holes having different radiuses. In particular, the holes 25 are each formed of a large through-hole 25a having a large radius and a small through-hole 25b having a radium smaller than that of the large hole 25a. The large hole 25a and the small hole 25b are arranged so that the central axis of the large hole 25a coincides with the central axis of the small hole 25b. That is, the holes 25 are each formed of the two holes having different sizes and penetrate the electrode support plate 20 in a thickness direction thereof. In addition, the large holes 25a are arranged at a main surface 22 side of the electrode support plate 20 which is in contact with the insulating plate 40. The small holes 25b are disposed at the other surface 23 side of the electrode support plate 20 facing the main surface 22.

When the first electrodes 31 are inserted into the respective holes 25, a side surface 31b of the first electrode 31 is partially brought into contact with an inside surface 20b of the small hole 25b. That is, the electrode support plate 20 supports the first electrode 31 by the inside surfaces 20b of the small holes 25b of the holes 25. In addition, the shape of the opening of the hole 25 is not limited to a round shape and, for example, may be an oval shape or a square shape.

In addition, at the other surface 23 side of the electrode support plate 20, a gas introduction hole 21 is formed around the small hole 25b. The gas introduction hole 21 is disposed, from the central axis of the hole 25, at a position longer than the distance corresponding to the radius of the small hole 25b and at a position equal to or shorter than the distance corresponding to the radius of the large hole 25a. In addition, the gas introduction hole 21 penetrates the electrode support plate 20 in the thickness direction thereof and is connected to the large hole 25a. In addition, the gas introduction hole 21 is connected to a gas supply tube 51 and functions to lead the first gas 12 supplied from the gas supply device 50 to the large hole 25a. In particular, when the first gas 12 is supplied, since the electrode support plate 20 supports the first electrode 31, the gas introduction hole 21 leads the first gas 12 to a gas supply hole 24 which is the space formed between the first electrode 31 and an inside surface 20a of the large hole 25a. That is, the gas introduction hole 21 is a through-hole penetrating the electrode support plate 20 so as to communicate between the gas supply hole 24 and the gas supply tube 51.

In this embodiment, the number of the gas introduction holes 21 provided around the small hole 25b is two. In addition, the number of the gas introduction holes 21 is not limited to that described above. At least one gas introduction hole 21 may be provided for each small hole 25b disposed at the other surface 23 side. In addition, the shape of the gas introduction hole 21 is not particularly limited as long as the first gas 12 supplied from the gas supply device 50 can be lead to the gas supply hole 24.

Heretofore, the electrode support plate 20 has been described. The primary purpose of the electrode support plate 20 is to support the first electrodes 31 and to form the gas supply holes 24 through which the first gas 12 is supplied. From this point of view, the electrode support plate 20 is not limited to a plate shape as long as having an electrode support function. In addition, for example, when the first electrode 31 is fixed to the insulating plate 40, and the first gas 12 is supplied to the space formed by the first electrode 31 and the insulating plate 40, the electrode support plate 20 is not always required.

[1-1-2. First Electrode]

The first electrodes 31 according to this embodiment are each an electrode having a cylindrical shape held by the corresponding hole 25 provided in the electrode support plate 20. For example, the first electrodes 31 are each held so as to be engaged in the corresponding small hole 25b provided at the other surface 23 side. The first electrodes 31 each function as a reaction electrode when multipoint generation of plasma is performed. In addition, the "cylindrical shape" indicates the concept in that the cross-section thereof includes besides a perfect circle and a rectangular shape, a shape having an error of several percentages. The shape of the first electrode 31 is not limited to a cylindrical shape and may be a rectangular column, a spherical shape, a conical shape, or the like.

In this embodiment, end surfaces 31a of the first electrodes 31 each face a first main surface 41 of the insulating plate 40 with a space interposed therebetween. That is, between the first electrode 31 and the insulating plate 40, the space is formed. In addition, the end surface 31a of the first electrode 31 and the first main surface 41 of the insulating plate 40 are disposed approximately in parallel to each other. That is, the minimum distance between the end surface 31a of the first electrode 31 and the first main surface 41 of the insulating plate 40 is approximately constant at any place. In addition, the side surface 31b of the first electrode 31 and the inside surface 20a of the large hole 25a of the electrode support plate 20 are disposed approximately in parallel to each other. That is, the minimum distance between the side surface 31b of the first electrode 31 and the inside surface 20a of the large hole 25a of the electrode support plate 20 is approximately constant at any place. Accordingly, the first gas 12 can be uniformly supplied to the gas supply holes 24, and the plasma 14 (see FIG. 7B) can be stably generated.

The first electrode 31 is formed for example, of a plasma-resistant metal material, such as tungsten or a tungsten alloy. As the first electrode 31, another plasma-resistant metal material may also be used, or although the durability is degraded, for example, copper, aluminum, iron, or an alloy thereof may also be used.

[1-1-3. Insulating Plate]

The insulating plate 40 is an insulating plate disposed between the first electrodes 31 and the space 81. In this embodiment, the insulating plate 40 is disposed so as to face the electrode support plate 20. In particular, the insulating plate 40 is in contact with the main surface 22 of the electrode support plate 20. As shown in FIG. 2, the insulating plate 40 has a first main surface 41 and a second main surface 42 which is a main surface opposite to the first main surface 41.

The insulating plate 40 is for example, an approximately rectangular flat plate. In addition, the shape of the insulating plate 40 is not limited to that described above, and any shape, such as a round shape or an oval shape, may also be used. The insulating plate 40 is formed for example, of an insulating material, such as an alumina ceramic.

The first main surface 41 is in contact with the electrode support plate 20. In particular, the first main surface 41 is disposed in contact with the main surface 22 of the electrode support plate 20. Accordingly, the distances between the first electrodes 31 and the respective second electrodes 32 can be set equivalent to each other, and hence the variation in impedance can be reduced.

The second main surface 42 is in contact with the space 81 in which the liquid 11 is received. That is, the second main surface 42 is exposed to the space 81 and is in contact with the liquid 11. In this embodiment, as shown in FIG. 2, the second electrodes 32 are disposed in contact with the second main surface 42.

The insulating plate 40 has a plurality of communication holes 43. The communication holes 43 are through-holes penetrating the insulating plate 40 at positions corresponding to those of the respective first electrodes 31 so as to communicate between the first electrodes 31 and the respective second electrodes 32 through the gas supply holes 24.

In particular, the communication holes 43 each penetrate the insulating plate 40 in the thickness direction thereof. The communication holes 43 are arranged in a two-dimensional manner when viewed in plan and are provided at positions corresponding to those of the respective first electrodes 31. In more particular, the communication holes 43 are provided so that the axes thereof coincide with the central axes of the respective first electrodes 31. For example, the axes of the communication holes 43 coincide with the axes of the respective holes 25 provided in the electrode support plate 20. That is, the first electrodes 31 are provided so as to correspond to the respective communication holes 43. Accordingly, even when an alternating-current voltage or a pulse voltage is applied between the first electrodes 31 and the second electrodes 32, a current can be allowed to uniformly flow between the electrodes through the communication holes 43.

The communication holes 43 are each for example, a cylindrical through-hole. The diameter of the communication hole 43 is for example, 10 to 250 μm.

The communication holes 43 are for example, processed by a hydrophilic treatment. In particular, when the insulating plate 40 in which the communication holes 43 are formed is processed by a plasma treatment, the communication holes 43 are processed by a hydrophilic treatment. The plasma treatment is for example, an atmospheric plasma treatment using an oxygen gas or a helium gas. When the communication holes 43 are hydrophilized, the liquid 11 to be received in the space 81 is likely to enter the communication holes 43. In addition, the hydrophilic treatment is not limited to a plasma treatment. For example, the insulating plate 40 in which the communication holes 43 are formed may be dipped in a predetermined chemical liquid so as to hydrophilize the communication holes 43.

In addition, for example, the diameters of the communication holes 43 may be increased so that the liquid 11 is likely to enter the holes 43. However, when the diameters of the communication holes 43 are excessively large (such as 700 μm), energy required for evaporation of the liquid 11 in the communication hole 43 is increased.

[1-1-4. Second Electrode]

The second electrodes 32 are disposed in the space 81 in which the liquid 11 is received. The second electrodes 32 are each disposed at a position in contact with the liquid 11 received in the space 81. In this embodiment, the second electrodes 32 are disposed in contact with the second main surface 42 of the insulating plate 40. The second electrodes 32 each function as a counter electrode to the first electrode 31 when plasma is generated.

The second electrode 32 is formed of an electrically conductive metal material. For example, the second electrode 32 is formed of tungsten, copper, aluminum, iron, an alloy thereof (such as stainless steel), or the like.

In this embodiment, the second electrodes 32 are provided so as to surround the respective communication holes 43. That is, the shape of each of the second electrodes 32 is an annular shape. The second electrodes 32 are each disposed so that the center of the annular shape thereof coincides with the central axis of the communication hole 43.

In addition, the number, the shape, and the arrangement of the second electrodes 32 are not limited to those described above. The second electrodes 32 may be disposed in the space 81 or may be disposed in contact therewith. That is, the second electrodes 32 each may be disposed so as to be at least partially exposed to the space 81 and to be in contact with the liquid 11.

For example, at least one second electrode 32 may be disposed at a position apart from the insulating plate 40. In addition, the second electrodes 32 are each not required to have an annular shape surrounding the communication hole 43 and each may be a cylindrical, a grating, or a flat electrode. For example, the second electrode 32 may be a flat electrode (in particular, having a shape similar to that of the electrode support plate 20) having through-holes, the size of each of which is one-size larger than that of the communication hole 43, provided at positions corresponding to those of the communication holes 43.

[1-1-5. Gas Supply Device]

The gas supply device 50 is connected to the gas supply holes 24 through the gas supply tube 51 and the gas introduction holes 21. The gas supply tube 51 is connected to the gas introduction holes 21 without any spaces interposed therebetween. That is, a gas other than the first gas 12 to be supplied through the gas supply tube 51 is not allowed to flow into the gas introduction holes 21. The gas supply device 50 supplies the first gas 12 to the gas supply holes 24 through the gas supply tube 51 and the gas introduction holes 21. The first gas 12 to be supplied is for example, air, nitrogen, or oxygen.

When air is used as the first gas 12, nitrogen radicals generated by performing discharge while air is supplied reacts with water, and nitrous acid and nitric acid are generated. That is, the liquid 11 is able to have a high water treatment performance.

When nitrogen is only used as the first gas 12, nitrogen radicals generated by performing discharge while nitrogen is supplied reacts with water, and nitrous acid and nitric acid are generated. That is, as is the case of using air, the same or a similar effect can be obtained.

When oxygen is only used as the first gas 12, although nitrogen components, such as nitrous acid, are not generated by performing discharge while oxygen is supplied, oxygen radicals and ozone are generated by discharge. Oxygen radicals have an oxidizing power, and ozone reacts with hydrogen peroxide to generate OH radicals (called advanced oxidation). Since having a strong oxidizing power, the OH radicals thus generated contributes to sterilization or decomposition of organic substances.

From those described above, when air, nitrogen, or oxygen is used as the first gas, strong sterilization or decomposition of organic substances can be obtained. In addition, in this embodiment, as the first gas 12, air which can be easily available is used.

The gas supply device 50 supplies the first gas 12 in the second period by the control of the control circuit 70. In addition, the gas supply device 50 stops the supply of the first gas 12 in the first period by the control of the control circuit 70. In addition, the gas supply device 50 always supplies the first gas 12 in the second period.

In addition, as the gas supply device 50, for example, a pump may be used. The flow rate of the first gas 12 supplied from the gas supply device 50 is not particularly limited, and a flow rate capable of filling the first gas 12 in the gas supply holes 24 may be good enough. In addition, in this embodiment, although the case in which the number of the gas supply device 50 is one is described by way of example, the number thereof is not limited to one. A plurality of gas supply devices 50 may also be provided. For example, the number of the gas supply devices 50 may be the same as the number of the first electrode 31.

[1-1-6. Power Source]

The power source 60 applies an alternating-current voltage or a pulse voltage between a plurality of electrode pairs 30 (between the first electrodes 31 and the respective second electrodes 32).

For example, the voltage to be applied is a voltage at which the electric field strength between the electrode pair 30 can be set to 2 to 50 kV/cm. In this embodiment, in accordance with the diameter of the communication hole 43, the voltage to be applied is determined. For example, when the diameter of the communication hole 43 is approximately 30 μm, the power source 60 applies a voltage of approximately 1.6 kV, and when the diameter of the communication hole 43 is approximately 10 μm, the power source 60 applies a voltage of approximately 600 V.

The voltage to be applied is for example, a high voltage pulse of 1 Hz to 100 kHz. The voltage waveform may be for example, any one of a pulse, a half-sine, and a sine waveform. In addition, a current flowing between the electrode pair 30 is for example, 1 mA to 1 A.

[1-1-7. Control Circuit]

The control circuit 70 is for example, a microcomputer or the like and is a processing portion which controls the operation of the plasma generating apparatus 10. In particular, the control circuit 70 controls the gas supply device 50 so as to supply the first gas 12. In addition, the control circuit 70 controls the power source 60 so as to apply an alternating-current voltage or a pulse voltage between the electrode pair 30. That is, the control circuit 70 controls ON and OFF of the supply of the first gas 12 by the gas supply device 50 and ON and OFF of the power source 60. Accordingly, the control circuit 70 (I), in the first period, generates the second gas 13 by evaporating the liquid 11 which enters the gas supply hole 24 through the communication hole 43 and generates the plasma 14 by performing discharge in the second gas 13 thus generated, and (II), in the second period after the first period, generates the plasma 14 by performing discharge in the first gas 12 supplied from the gas supply device 50 through the gas supply hole 24.

In addition, in this embodiment, the second period is started in accordance with the concentration of hydrogen peroxide in the liquid 11 detected by the hydrogen peroxide sensor 90.

[1-1-8. Liquid Holding Portion]

The liquid holding portion 80 has the space 81 holding the liquid 11. The space 81 is filled, for example, with the liquid 11. In particular, the liquid holding portion 80 is for example, a storage bath (tank) or a pipe arrangement in which the liquid 11 is received. That is, the space 81 is an inside space of the storage bath or the pipe arrangement. The liquid 11 received in the space 81 may be either static water or dynamic water (flowing water).

In addition, the wall surface of the storage bath or the pipe arrangement may partially function as the insulating plate 40. That is, the liquid holding portion 80 may include the insulating plate 40.

In addition, the wall surface of the storage bath or the pipe arrangement may partially function as the second electrode 32. That is, the liquid holding portion 80 may include at least one second electrode 32.

In addition, in order to prevent an electric shock, the liquid holding portion 80 may be grounded.

[1-1-9. Hydrogen Peroxide Sensor]

The hydrogen peroxide sensor 90 is a sensor measuring the concentration of hydrogen peroxide contained in the liquid 11 and is connected to the control circuit 70. The hydrogen peroxide sensor 90 measures the concentration of hydrogen peroxide in the liquid 11 in the first period and the second period, each of which is to be described later. The measurement of the concentration of hydrogen peroxide may be performed either at a real time or at predetermined intervals.

In this embodiment, the hydrogen peroxide sensor 90 is provided at an upper portion (the surface of the liquid holding portion 80 facing the second main surface 42 of the insulating plate 40) of the liquid holding portion 80. In addition, the position at which the hydrogen peroxide sensor 90 is provided is not limited to that described above. The hydrogen peroxide sensor 90 may be disposed in the space 81 of the liquid holding portion 80 so as to be in contact with the liquid 11. In addition, the number of the hydrogen peroxide sensors 90 to be provided may be either one or at least two. For example, the number of the hydrogen peroxide sensors 90 may be the same as the number of the electrode pairs 30. Accordingly, the degree of uniformity of the concentration of hydrogen peroxide in the liquid 11 can be measured.

[1-2. Operation]

Next, the operation of the plasma generating apparatus 10 according to this embodiment will be described with reference to FIGS. 4 to 8.

Figure 4:
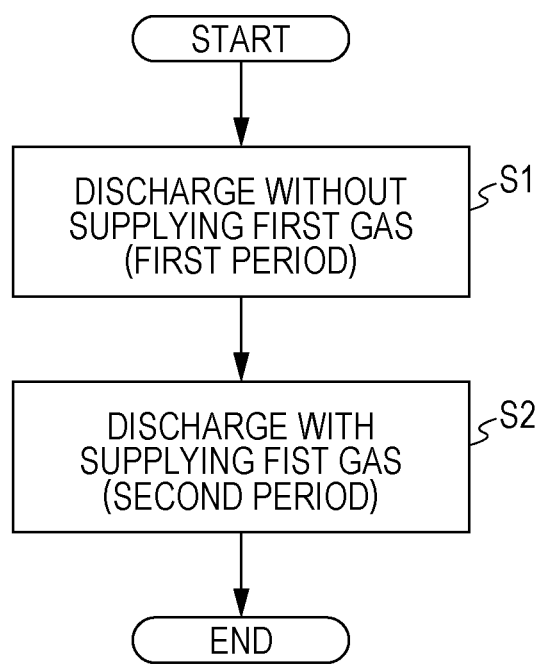
FIG. 4 is a flowchart showing an operation of the plasma generating apparatus according to the embodiment.
Figure 5A:
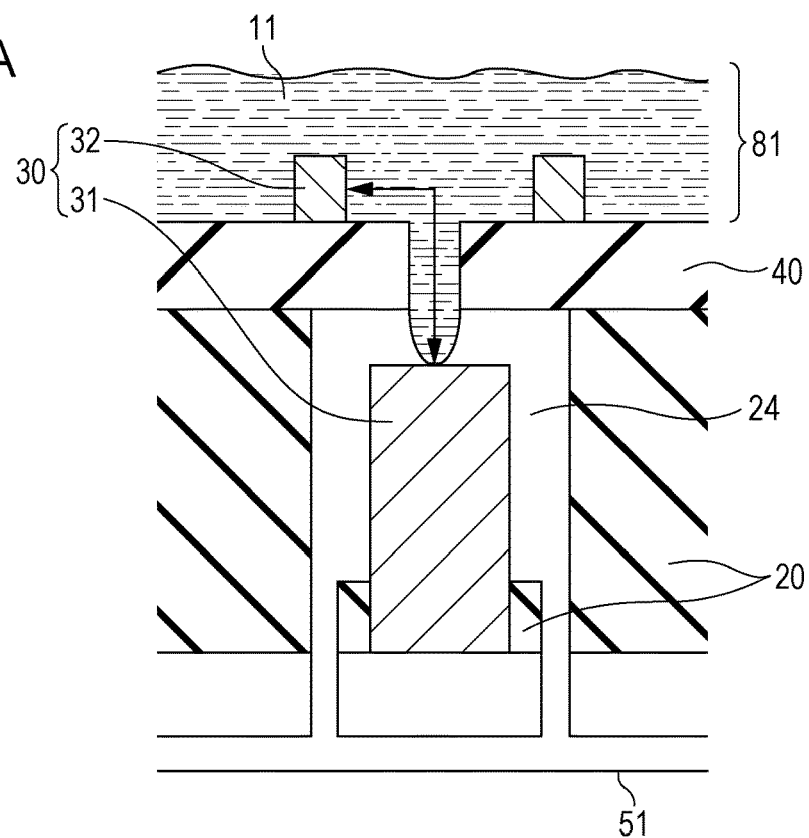
FIG. 5A is a schematic view showing the state in which a current path is formed in a first period in the plasma generating apparatus according to the embodiment.
Figure 5B:
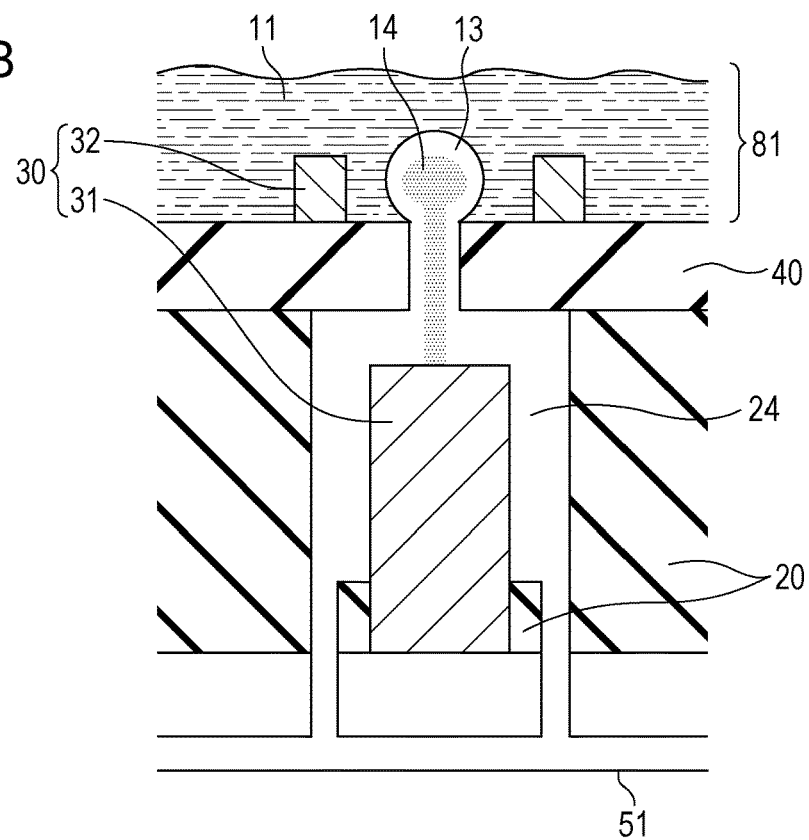
FIG. 5B is a schematic view showing the state of generation of plasma in the first period in the plasma generating apparatus according to the embodiment.
Figure 6:
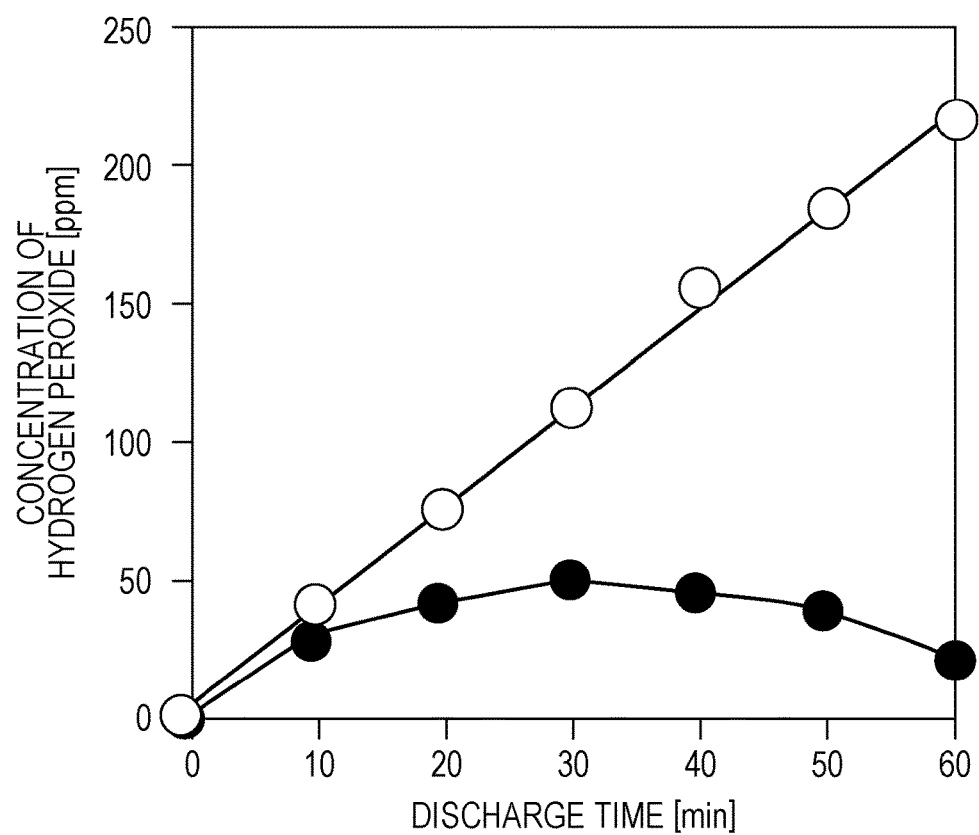
FIG. 6 is a graph showing measurement results of the concentration of hydrogen peroxide with respect to a discharge time of the plasma generating apparatus according to the embodiment.
Figure 7A:
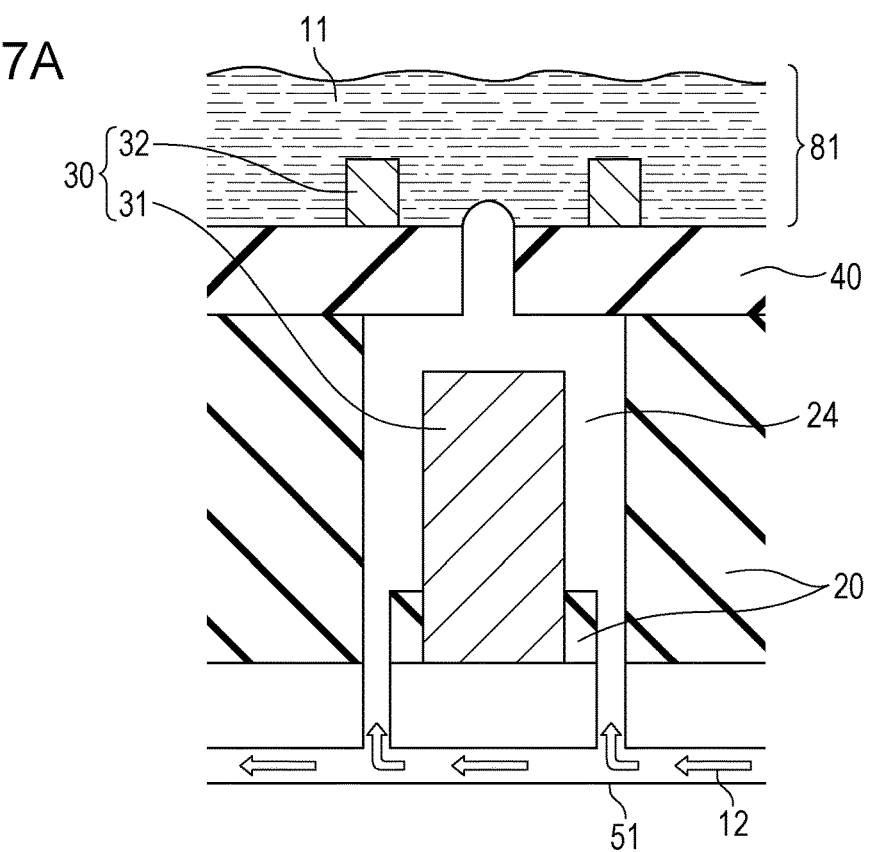
FIG. 7A is a schematic view showing the state in which the current path is broken in a second period in the plasma generating apparatus according to the embodiment.
Figure 7B:
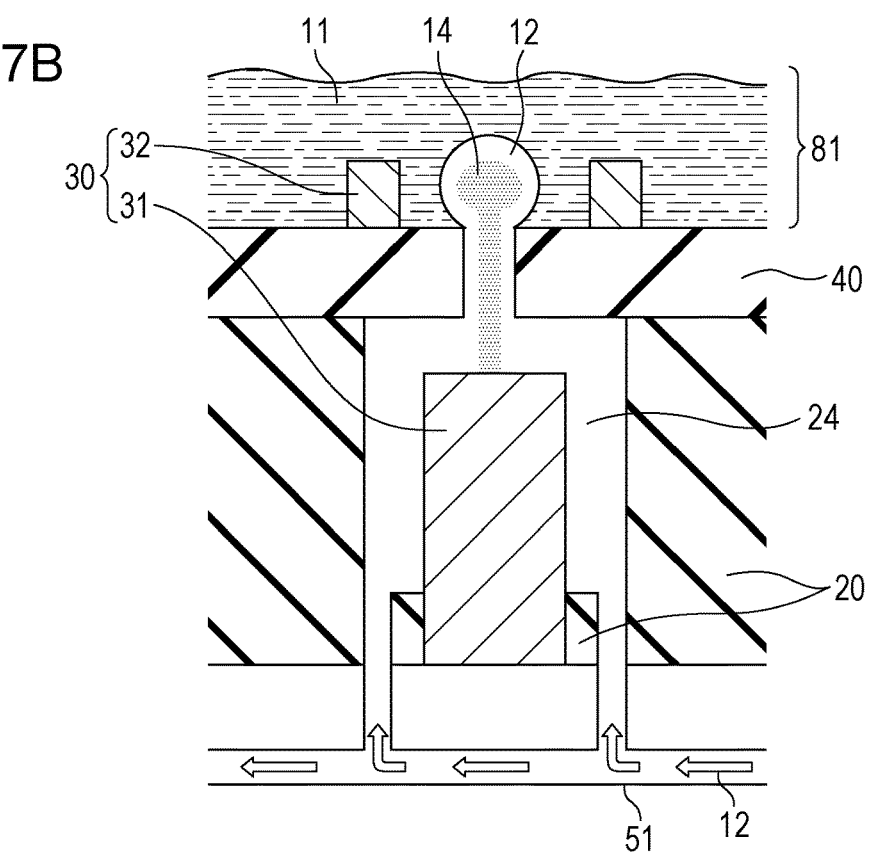
FIG. 7B is a schematic view showing the state of generation of plasma in the second period in the plasma generating apparatus according to the embodiment.

FIG. 4 is a flowchart showing the operation of the plasma generating apparatus 10 according to this embodiment. FIG. 5A is a schematic view showing the state in which a current path is formed in the first period in the plasma generating apparatus 10 according to this embodiment. FIG. 5B is a schematic view showing the state in which the plasma 14 is generated in the first period in the plasma generating apparatus 10 according to this embodiment. FIG. 6 is a graph showing measurement results of the concentration of hydrogen peroxide with respect to a discharge time of the plasma generating apparatus 10 according to this embodiment. FIG. 7A is a schematic view showing the state in which the current path is broken in the second period in the plasma generating apparatus 10 according to this embodiment. FIG. 7B is a schematic view showing the state in which the plasma 14 is generated in the second period in the plasma generating apparatus 10 according to this embodiment. In addition, in FIGS. 5A, 5B, 7A, and 7B, although one first electrode 31 will be described, in this embodiment, a phenomenon similar to that described below is generated in each of the first electrodes 31, and the plasma 14 can be generated at a plurality of points.

As shown in FIG. 4, in the first period, the operation of the plasma generating apparatus 10 according to this embodiment is to apply an alternating-current voltage or a pulse voltage between the electrode pair 30 without supplying the first gas 12 from the gas supply device 50 (S1). In addition, in the second period after the first period, the first gas 12 is supplied from the gas supply device 50, and an alternating-current voltage or a pulse voltage is applied between the electrode pair 30 (S2). The first period, the second period, and the switching therebetween will be described in detail.

[1-2-1. First Period]

First, as shown in FIG. 4, the control circuit 70 controls the gas supply device 50 not to supply the first gas 12 and controls the power source 60 to apply an alternating-current voltage or a pulse voltage between the electrode pairs 30 (S1). In addition, the alternating-current voltage or the pulse voltage to be applied is applied to the electrode pairs 30 under the same condition. Hereinafter, the operation will be described in detail.

When the alternating-current voltage or the pulse voltage is applied between the electrode pair 30, the liquid 11 enters the communication hole 43. For example, since the alternating-current voltage or the pulse voltage is applied between the electrode pair 30, the electric field is generated between the electrode pair 30, and the liquid 11 is polarized. Accordingly, the liquid 11 is pulled by the first electrode 31 and enters the communication hole 43. In addition, for example, when the communication hole 43 is processed by a hydrophilic treatment, independent of the application of the voltage, the liquid 11 may enter the communication hole 43 in some cases.

The liquid 11 which enters the communication hole 43 enters the gas supply hole 24 as shown in FIG. 5A and is brought into contact with the first electrode 31. Accordingly, between the electrode pair 30, a current path (two arrows in the figure) is formed by the liquid 11 which enters the communication hole 43.

When the current path is formed, a current flows between the electrode pair 30, so that heat is generated. By the heat thus generated, the liquid 11 which enters the gas supply hole 24 through the communication hole 43 is evaporated, and hence the second gas 13 is generated.

As shown in FIG. 5B, since the second gas 13 thus generated covers the periphery of the first electrode 31, the current path formed between the electrode pair 30 is broken, and discharge occurs in the second gas 13, so that the plasma 14 is generated. Accordingly, since the plasma 14 is generated in the second gas 13, oxidizing radicals containing OH radicals are generated. The oxidizing radicals thus generated are diffused in the liquid 11. Since the oxidizing radicals each have a strong oxidizing power, organic substances in the liquid 11 are partially oxidation-decomposed by the oxidizing radicals. Together with this oxidation reaction, OH radicals of the oxidizing radicals are bonded to each other in the liquid 11 to generate hydrogen peroxide. In addition, the hydrogen peroxide thus formed is stored in the liquid 11. That is, the first period is a period in which hydrogen peroxide is stored.

Since having a strong oxidizing power, the oxidizing radicals containing OH radicals performs, within a short time, sterilization or decomposition of organic substances. That is, the oxidizing radicals have a short life. For example, the life of OH radicals is approximately one millionth of a second. That is, when being generated, at the same time, the OH radicals are changed into different substances. However, in terms of the sterilization or the decomposition of organic substances, the oxidizing radicals are preferably stably present in the liquid 11. That is, when a water treatment is performed, the oxidizing radicals are preferably present in the liquid 11. Hence, in this embodiment, hydrogen peroxide generated by bonding between OH radicals is used. Since having a weak oxidizing power, hydrogen peroxide is stable and has a long life. In addition, when an alternating-current voltage or a pulse voltage is applied to a liquid 11 containing hydrogen peroxide, oxidizing radicals containing OH radicals are generated by decomposition of hydrogen peroxide. That is, hydrogen peroxide is stored in the liquid 11, and when sterilization or decomposition of organic substances is performed, the liquid 11 containing hydrogen peroxide is discharged to generate oxidizing radicals containing OH radicals, so that the sterilization or the decomposition of organic substances can be efficiently performed. Hence, the storage of hydrogen peroxide is significantly important for the sterilization or the decomposition of organic substances.

Next, with reference to FIG. 6, the relationship between a storage amount of hydrogen peroxide and a discharge time in the first period will be described. The vertical axis and the horizontal axis of FIG. 6 represent the concentration [ppm] of hydrogen peroxide and the discharge time [min], respectively. The amount of the liquid 11 used in the experiment is 50 ml, and the electric conductivity of the liquid 11 is 20 mS/m. In addition, as discharge conditions, the number of the electrode pairs 30 is 9 (that is, the number of discharge points is 9), a consumption electric power (electric power supplied to the first electrode 31) of the power source 60 is 20 W. In addition, the graph of FIG. 6 is one example showing the relationship between the concentration of hydrogen peroxide and the discharge time with or without the supply of the first gas 12. In accordance with the volume of the liquid, the number of the electrode pairs 30, and the like, the relationship between the concentration of hydrogen peroxide and the discharge time is changed.

White circles of FIG. 6 represent the relationship between the concentration of hydrogen peroxide and the discharge time in the case in which discharge is performed without supplying the first gas 12. That is, the relationship between the concentration of hydrogen peroxide and the discharge time in the first period is shown. From the result shown in FIG. 6, it is found that in the first period, the concentration of hydrogen peroxide is increased proportional to the discharge time. That is, it is found that in the first period, hydrogen peroxide is stored in the liquid 11. This proportional relationship between the concentration of hydrogen peroxide and the discharge time is the same even if the volume of the liquid and the discharge conditions are changed. That is, in the first period, when the discharge time is increased, the concentration of hydrogen peroxide stored in the liquid 11 can be easily increased.

Black circles of FIG. 6 shows one example of the relationship between the concentration of hydrogen peroxide and the discharge time in the second period which will be described below. In addition, in the second period, as the first gas 12 to be supplied from the gas supply device 50, air is used. From FIG. 6, it is found that in the second period, the relationship between the concentration of hydrogen peroxide and the discharge time is not a proportional relationship, and the concentration of hydrogen peroxide is not increased as the discharge time is increased. In the second period, when the discharge time reaches approximately 30 minutes or more, the concentration of hydrogen peroxide is decreased as the discharge time is increased. The reason for this is believed that hydrogen peroxide is consumed by a reaction with nitrous acid or the like generated in the second period. That is, in the second period, hydrogen peroxide cannot be efficiently stored.

As described above, when an alternating-current voltage or a pulse voltage is applied between the electrode pair 30 without supplying the first gas 12, hydrogen peroxide, which is a significantly important substance in view of the sterilization or the decomposition of organic substances, can be efficiently stored in the liquid 11.

[1-2-2. Second Period]

The control circuit 70 starts the second period after hydrogen peroxide is stored in the first period.

First, as shown in FIG. 4, the control circuit 70 controls the gas supply device 50 to supply the first gas 12 and controls the power source 60 to apply an alternating-current voltage or a pulse voltage between the electrode pair 30 (S2). Hereinafter, the operation will be described in detail. In addition, in this embodiment, the electrode pair 30 used in the second period is the same as the electrode pair 30 used in the first period. That is, the electrode pair 30 used in the first period may also be used in the second period. Accordingly, the number of the electrode pairs 30 can be reduced. In addition, the application of the alternating-current voltage or the pulse voltage between the electrode pair 30 in the second period is performed under the same condition as that of the application performed in the first period. That is, regardless of the first period and the second period, the power source 60 applies a predetermined alternating-current voltage or pulse voltage between the electrode pair 30. Accordingly, the number of the power sources 60 can be reduced. The condition of the voltage applied by the power source 60 is not limited to that described above. The condition of the alternating-current voltage or the pulse voltage applied between the electrode pair 30 in the first period may be changed from that in the second period. In addition, the number of the power sources 60 may also be at least two.

In the second period, the control circuit 70 instructs the gas supply device 50 to supply the first gas 12 to the gas supply hole 24 through the gas supply tube 51 and the gas introduction hole 21. In addition, in this embodiment, as the first gas 12 to be supplied from the gas supply device 50 in the second period, air is used. In addition, until the first gas 12 is filled in the gas supply hole 24 (until the current path between the electrode pair 30 is broken), the control circuit 70 instructs the power source 60 not to apply the voltage to the electrode pair 30.

When the second period is started, the control circuit 70 instructs the gas supply device 50 to supply the first gas 12. The supply of the first gas 12 is performed to the first electrodes 31 at approximately uniform flow rates. The first gas 12 supplied from the gas supply device 50 is supplied in the form of air bubbles to the gas supply hole 24 through the gas supply tube 51 and the gas introduction hole 21. The flow rate of the first gas 12 to be supplied is not particularly limited. The flow rate of the first gas 12 may be good enough when the gas supply hole 24 is filled therewith.

The first gas 12 thus supplied fills the gas supply hole 24 and covers the periphery of the first electrode 31. Accordingly, the current path formed between the electrode pair 30 is broken. FIG. 7A is a schematic view showing the state in which for example, the first gas 12 is filled in the gas supply hole 24 and the communication hole 43 and partially protrudes into the space 81. When the current path is broken, the control circuit 70 instructs the power source 60 to start the application of the voltage to the electrode pair 30. In addition, as shown in FIG. 7B, discharge occurs in the first gas 12, and the plasma 14 is generated. In addition, in the second period, while the plasma 14 is generated, the supply of the first gas 12 is continued.

By the alternating-current voltage or the pulse voltage applied in the presence of the liquid 11 containing hydrogen peroxide stored in the first period, oxidizing radicals containing OH radicals are generated. The oxidizing radicals containing OH radicals thus generated are diffused in the liquid 11, and the sterilization of the liquid 11 or the decomposition of organic substances is performed. That is, since the oxidizing radicals are generated using the hydrogen peroxide generated in the first period, the second period is a period in which the sterilization of the liquid 11 or the decomposition of organic substances is performed.

Hereinafter, the decomposition rate of organic substances in the second period will be described with reference to FIG. 8. FIG. 8 is a graph showing a measurement result of an indigo carmine decomposition rate with respect to an initial concentration of hydrogen peroxide in the case in which a test liquid is prepared by dissolving indigo carmine in a liquid having a controlled initial concentration of hydrogen peroxide, and the second period is then started. In FIG. 8, the vertical axis represents the decomposition rate [ppm/min] of indigo carmine, and the horizontal axis represents the initial concentration [ppm] of hydrogen peroxide. The initial concentration of hydrogen peroxide indicates the concentration of hydrogen peroxide in the test liquid right before the start of the second period. In particular, the initial concentrations of hydrogen peroxide are set to 3, 30, 300, and 3,000 ppm. In addition, the horizontal axis represents the logarithmic scale.

Indigo carmine is a water-soluble organic substance and has been frequently used as a wastewater treatment model. The initial concentration of indigo carmine of an aqueous solution used in this experiment is 10 ppm, the water volume is 100 ml, and the electric conductivity is 20 mS/m. The initial concentration of indigo carmine is the concentration dissolved in the test liquid right before the start of the second period. In addition, as the discharge conditions, the number of the electrode pairs 30 is 9 (that is, the number of discharge points is 9), and the consumption electric power (electric power supplied to the first electrode 31) of the power source is 30 W.

From FIG. 8, it is found that as the initial concentration of hydrogen peroxide is increased, the decomposition rate of indigo carmine is increased. When the initial concentration of hydrogen peroxide is 10 ppm or more, the decomposition rate of indigo carmine is more increased. In particular, when the initial concentration of hydrogen peroxide is in a range of from 30 to 300 ppm, the change in decomposition rate of indigo carmine with respect to the initial concentration of hydrogen peroxide becomes steeper. In addition, when the initial concentration of hydrogen peroxide is 0 ppm, the decomposition rate of indigo carmine is approximately 0.49 ppm/min. From FIG. 8, it is found that since hydrogen peroxide is contained, although the amount thereof is very small, in the liquid 11 (that is, since oxidizing radicals are generated by decomposition of hydrogen peroxide), compared to the case in which no hydrogen peroxide is contained, the decomposition rate of indigo carmine is increased. In particular, from FIG. 8, it is found that even when the initial concentration of hydrogen peroxide is low, such as approximately 3 ppm, a decomposition rate of indigo carmine of 0.54 ppm/min, which is higher than the decomposition rate of indigo carmine when the initial concentration of hydrogen peroxide is 0 ppm, can be obtained.

In addition, in FIG. 8, the result obtained by decomposition of indigo carmine using hydrogen peroxide itself is shown as reference (Reference in FIG. 8). In this case, the result obtained by decomposition of indigo carmine using hydrogen peroxide itself is a result of measurement of the decomposition rate of indigo carmine obtained by hydrogen peroxide in the case in which hydrogen peroxide is stored in the liquid 11, and no discharge is performed. In addition, the initial concentration of hydrogen peroxide is set to 3,000 ppm.

As shown in FIG. 8, although the initial concentration of hydrogen peroxide is set to 3,000 ppm, by hydrogen peroxide itself, indigo carmine is hardly decomposed. In particular, the decomposition rate of indigo carmine is very low, such as 0.1 ppm/min or less. From the results described above, in the second period, the generation of oxidizing radicals containing OH radicals from hydrogen peroxide by discharge is significantly important in terms of the sterilization of the liquid 11 or the decomposition of organic substances. In addition, from the result in that indigo carmine cannot be decomposed by hydrogen peroxide itself, it can also be said that hydrogen peroxide contained in the liquid 11 is stable.

As described above, in the second period, since the oxidizing radicals containing OH radicals are generated from hydrogen peroxide by discharge while the first gas 12 is supplied, the sterilization or the decomposition of organic substances can be efficiently performed.

[1-2-3. Timing of Start of Second Period after First Period]

In this embodiment, the concentration of hydrogen peroxide is measured by the hydrogen peroxide sensor 90. As described above, the first period is a period in which hydrogen peroxide is stored in the liquid 11. The hydrogen peroxide sensor 90 measures the concentration of hydrogen peroxide in the liquid 11 in the first period. The concentration of hydrogen peroxide may be measured either at a real time or at predetermined intervals. The concentration of hydrogen peroxide thus measured is sent to the control circuit 70. When the control circuit 70 determines the concentration of hydrogen peroxide sent from the hydrogen peroxide sensor 90 as a predetermined value or more, after the first period is finished, the second period is started. That is, the period in which hydrogen peroxide is stored is finished, and the period in which by the use of the hydrogen peroxide, oxidizing radicals containing OH radicals are generated is started. From the decomposition rate of indigo carmine shown in FIG. 8, the concentration of hydrogen peroxide stored in the liquid 11 in the first period may be set to be high. As shown in FIG. 8, when the concentration is 10 ppm or more, since the decomposition rate of indigo carmine is increased, the predetermined value may be set to 10 ppm.

Since the decomposition rate is further increased, the predetermined value may also be set to 30 ppm. In addition, the predetermined value is not limited to those mentioned above.

In addition, as apparent from the decomposition rate of indigo carmine shown in FIG. 8, as long as hydrogen peroxide is stored although the amount thereof is small, compared to the case in which no hydrogen peroxide is stored (0 ppm), the decomposition rate of indigo carmine is increased. From the result described above, after the first period is finished, the second period may be started without measuring the concentration of hydrogen peroxide. For example, as is the example of the relationship between the concentration of hydrogen peroxide and the discharge time shown in FIG. 6, from the relationship between the concentration of hydrogen peroxide and the discharge time of a plasma generating apparatus to be used, the discharge time may be controlled in the first period. That is, when it is known that in the first period, a predetermined concentration (such as 10 ppm) of hydrogen peroxide is obtained by performing discharge for a predetermined time (such as 30 minutes), after the first period passes for the above predetermined time, the second period may be started.

[1-3. Effects and the Like]

As described above, the plasma generating apparatus 10 according to this embodiment comprises at least one electrode pair 30 generating the plasma 14 in the liquid 11 or in the vicinity thereof, the power source 60 applying a voltage to the at least one electrode pair 30, the gas supply device 50 supplying the first gas 12 to the liquid 11, and the control circuit 70 controlling the operations of the power source 60 and the gas supply device 50. The control circuit 70 (I) instructs, in the first period, the gas supply device 50 not to supply the first gas 12 and the power source 60 to apply a voltage to the at least one electrode pair 30 so as to generate the plasma 14 in the second gas 13 generated by evaporation of the liquid 11, and (II) instructs, in the second period after the first period, the gas supply device 50 to supply the first gas 12 in the liquid 11 and the power source 60 to apply a voltage to the at least one electrode pair 30 so as to generates plasma in the first gas 12.

Accordingly, by a simple control in which the first gas 12 is supplied or not from the gas supply device 50, a liquid 11 having a high oxidizing power can be generated. In particular, in the first period, by performing discharge without supplying the first gas 12 from the gas supply device 50, hydrogen peroxide can be efficiently stored. In addition, in the second period, by performing discharge while the first gas 12 is supplied from the gas supply device 50, oxidizing radicals containing OH radicals can be efficiently generated using the above hydrogen peroxide. Accordingly, since the sterilization of the liquid or the decomposition of organic substances can be efficiently performed, the plasma generating apparatus is able to have a high water treatment performance. In addition, since the storage of hydrogen peroxide and the generation of a high oxidizing liquid 11 containing OH radicals can be performed by one treatment bath, the size of the plasma generating apparatus can be reduced.

Modified Example

Hereinafter, with reference to FIG. 9, a modified example of the embodiment will be described.

[2-1. Structure]

Since the structure of a plasma generating apparatus 10 according to a modified example of the embodiment is the same as the structure (FIG. 1) of the embodiment, description will be omitted or simplified. A point different from the embodiment is that a control circuit 70 controls besides a first period and a second period, a period in which no discharge is performed, and this different point will be described below.

[2-2. Operation]

Figure 9:
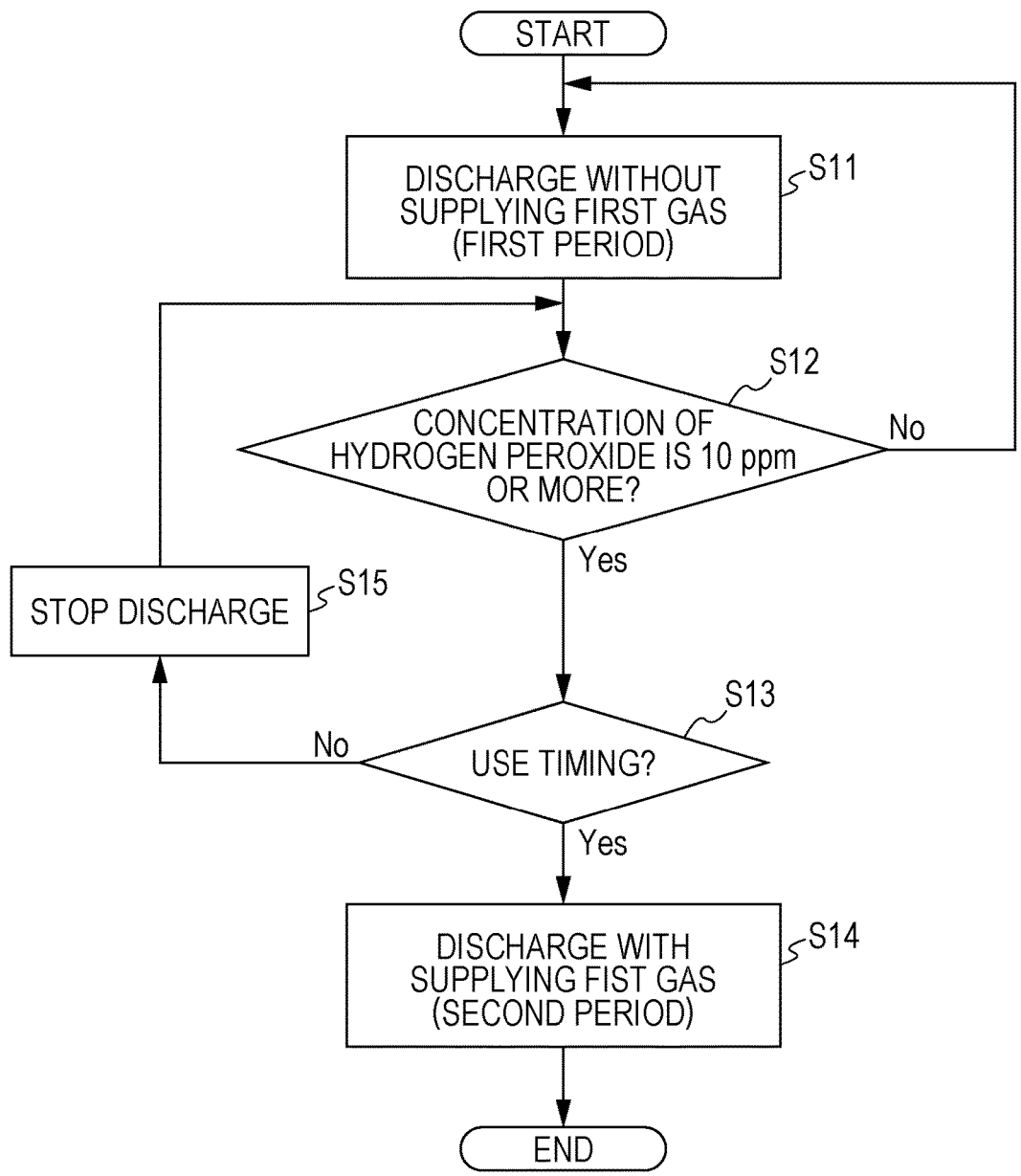
FIG. 9 is a flowchart showing an operation of a plasma generating apparatus according to a modified example.

FIG. 9 is a flowchart showing an operation of the plasma generating apparatus 10 according to the modified example of the embodiment. An operation of a first period (S11) and an operation of a second period (S14) are the same as the operations of the embodiment, and detailed description thereof will be omitted.

First, as the operation of the plasma generating apparatus 10 according to this modified example, as shown in FIG. 9, in the first period, without supplying a first gas 12 from a gas supply device 50, a power source 60 is controlled to apply an alternating-current voltage or a pulse voltage between an electrode pair 30 (S11), and hydrogen peroxide is stored in a liquid 11. In this case, when the concentration of hydrogen peroxide stored in the liquid 11 is 10 ppm or more (Yes in S12), whether it is a use timing or not is determined (S13). In this step, the use timing is a timing at which sterilization of the liquid 11 itself or decomposition of organic substances is started. Alternatively, the use timing is a timing at which by the use of a liquid 11 containing oxidizing radicals (that is, by the use of a liquid 11 processed by a plasma treatment), sterilization of another liquid or gas or decomposition of organic substances is started.

The determination of the concentration of hydrogen peroxide is performed by the control circuit 70. In the modified example of the embodiment, the control circuit 70 performs the determination from the concentration of hydrogen peroxide measured by a hydrogen peroxide sensor 90. The measurement of the concentration of hydrogen peroxide may be performed either at a real time or at predetermined intervals. In addition, the determination of the concentration of hydrogen peroxide may not be performed using the hydrogen peroxide sensor 90, and for example, the concentration of hydrogen peroxide may be determined by controlling a discharge time in the first period.

When the concentration of hydrogen peroxide is lower than 10 ppm (No in S12), the first period (S11) in which discharge is performed without supplying the first gas 12 is continued. Since the step S12 of determining the concentration of hydrogen peroxide is provided, the efficiency of a water treatment, such as the sterilization of the liquid 11 or the decomposition of organic substances, performed by oxidizing radicals containing OH radicals in the second period can be controlled (see FIG. 8). In addition, the concentration of hydrogen peroxide used as the determination standard in the step S12 is not limited to 10 ppm. The concentration of hydrogen peroxide used as the determination standard is set if necessary. For example, as the determination standard, instead of using a concentration of hydrogen peroxide of 10 ppm, a concentration of hydrogen peroxide of 30 ppm may also be used at which the decomposition rate of indigo carmine is further increased. In addition, another concentration of hydrogen peroxide may also be used.

When the concentration of hydrogen peroxide is determined to be 10 ppm or more, next, whether it is the use timing or not is determined (S13). Since the case in which although the concentration of hydrogen peroxide is 10 ppm or more, it is not a desirable use timing may occur in some cases, whether the second period may be started or not is determined. In addition, for example, the determination may be performed by the control of a predetermined time using a timer or the like. In particular, after the concentration of hydrogen peroxide reaches 10 ppm or more, the second period may be started after a certain period of time passes therefrom, or the second period may be started when it reaches a predetermined time. Alternatively, a user may determine whether it is the use timing or not. In this case, the user instructs whether to start the second period or not.

When it is the use timing (Yes in S13), the control circuit 70 controls the gas supply device 50 to supply the first gas 12 and the power source 60 to apply an alternating-current voltage or a pulse voltage between the electrode pair 30, so that the second period is started (S14). That is, by the use of hydrogen peroxide generated in the first period, oxidizing radicals containing OH radicals are generated, and a water treatment, such as sterilization or decomposition of organic substances, is performed.

In the case in which it is not the use timing (No in S13), the control circuit 70 controls the power source 60 to stop the application of the voltage to the electrode pair 30 (S15). Since having a long life as compared to that of oxidizing radicals containing OH radicals, hydrogen peroxide can be stored in the liquid 11 by stopping the discharge. That is, by stopping the discharge when it is not the use timing, when the use timing comes, oxidizing radicals containing OH radicals can be efficiently generated. In addition, since the discharge can be stopped until the use timing comes, the electric power can be reduced.

The half life of the concentration of hydrogen peroxide generated in the first period is approximately 15.7 days. For example, when the discharge is stopped when the concentration of hydrogen peroxide is 20 ppm, in the liquid 11, 10 ppm or more of hydrogen peroxide is contained for approximately 15.7 days. Hence, within 15.7 days after the discharge is stopped, when the second period is started, a liquid 11 having a high oxidizing power can be efficiently generated. In addition, if approximately 15.7 days or more passes from the stop of the discharge, the concentration of hydrogen peroxide in the liquid 11 may be decreased to less than 10 ppm in some cases. Hence, by measuring the concentration of hydrogen peroxide, whether the concentration of hydrogen peroxide is 10 ppm or more or not is determined. When the concentration of hydrogen peroxide thus measured is less than 10 ppm, the first period is again started. That is, the storage of hydrogen peroxide is performed. Accordingly, even in the state in which the discharge is stopped, the concentration of hydrogen peroxide can be maintained at 10 ppm or more. Hence, when the second period is started, since oxidizing radicals containing OH radicals can be efficiently generated, the sterilization or the decomposition of organic substances can be performed at a high rate. That is, a high water treatment performance can be obtained.

In addition, as described above, although being set to 10 ppm, the determination standard of the concentration of hydrogen peroxide is not limited thereto. For example, the determination standard of the concentration of hydrogen peroxide may be set to 30 ppm or may also be set to another value. In addition, although the measurement of the concentration of hydrogen peroxide is performed after the half life of hydrogen peroxide passes, the measurement is not limited thereto. After the discharge is stopped, the measurement of the concentration of hydrogen peroxide may be performed either at a real time or at predetermined intervals. In addition, the measurement of the concentration of hydrogen peroxide may not be performed. For example, when a decreased amount (such as the half life) of hydrogen peroxide is known with respect to a time period in which the discharge is stopped, from the concentration of hydrogen peroxide at which the discharge is stopped and the decreased amount of the hydrogen peroxide, a time at which although the discharge is stopped, the concentration of hydrogen peroxide is 10 ppm or more is calculated, and when the time thus calculated passes from the stop of the discharge, the first period may be again started.

[2-3. Effects and the Like]

As described above, after the first period is finished, and before the second period is started, the control circuit 70 instructs the power source 60 to stop the application of the voltage to at least one electrode pair 30.

Accordingly, in the case in which although the first period is finished, it is not a timing (use timing) to start the second period, hydrogen peroxide generated in the first period can be stored in the liquid 11. Hydrogen peroxide has a lower oxidizing power than that of oxidizing radicals containing OH radicals and is stabler than that. Hence, hydrogen peroxide can be stored in the liquid 11 for a certain period of time. Hence, even in the case in which the timing to start the second period comes, since hydrogen peroxide is contained in the liquid 11, oxidizing radicals containing OH radicals can be efficiently generated. That is, a liquid 11 having a high oxidizing power can be efficiently generated. Hence, since the sterilization of the liquid 11 or the decomposition of organic substances can be efficiently performed, the plasma generating apparatus is able to have a high water treatment performance. In addition, since the discharge is stopped until the use timing comes, the electric power can be reduced.

In addition, in the period in which the voltage application is stopped, the control circuit 70 further determines whether the concentration of hydrogen peroxide in the liquid 11 is lower than a predetermined value or not, and when the concentration of hydrogen peroxide is determined to be lower than the predetermined value, the first period is again started.

Accordingly, even if the concentration of hydrogen peroxide is decreased when the discharge is stopped, since the first period is again started, the concentration of hydrogen peroxide can be maintained at a predetermined value or more. Hence, even when the use timing comes, and the second period is started, since hydrogen peroxide is contained in the liquid 11 at a predetermined value or more, the sterilization of the liquid or the decomposition of organic substances can be performed at a high rate. Hence, the plasma generating apparatus is able to have a high water treatment performance.

Other Embodiments

Heretofore, although the plasma generating apparatus according to at least one aspect has been described with reference to the embodiments, the present disclosure is not limited to those embodiments. As long as within the scope of the present disclosure, various modifications of the embodiment performed by a person skilled in the art and various modes formed in combination of constituent elements of different embodiments are also included in the scope of the present disclosure.

For example, in the above embodiment, although the first gas 12 is supplied to the first electrode 31 through the gas introduction hole 21 and the gas supply hole 24, the structure is not limited to that described above. For example, the first electrode 31 may have a cylindrical through-hole, the through-hole may be connected to the gas supply device 50 with the gas supply tube 51 interposed therebetween, and the first gas 12 may be supplied from the through-hole. Accordingly, since the flow rate of the first gas 12 to be supplied can be reduced, the size of the gas supply device 50 can be reduced.

In addition, for example, although the example in which the number of the electrode pairs 30 is 9 is described above, the number of the electrode pairs 30 is not limited thereto. For example, the number of the electrode pairs 30 may be either 1 or 9 or more. Accordingly, in accordance with the volume of the liquid 11, the number of the electrode pairs 30 can be appropriately selected.

In addition, for example, the plasma generating apparatus 10 may comprise no liquid holding portion 80. For example, the plasma generating apparatus 10 may be used by being connected to a treatment bath or a pipe arrangement disposed outside. Accordingly, the plasma generating apparatus 10 may be used for various treatment baths or pipe arrangements.

In addition, for example, the electrode pairs 30 may be disposed in the liquid 11.

In addition, within the scope of Claims or the scope of the equivalent thereto, various modifications, replacements, additions, omissions, and the like may be performed on the above embodiments.

What is claimed is:

1. A plasma generating method, used in a plasma generating apparatus which includes a container, a first electrode, and a second electrode, the method comprising:
   supplying a liquid in the container so that the second electrode is in contact with the liquid;
   in a first period, generating first plasma in a bubble generated in the liquid by applying a first voltage between the first electrode and the second electrode;
   supplying a first gas in the liquid in a second period after the first period; and
   generating second plasma in the first gas by applying a second voltage between the first electrode and the second electrode, wherein:
   in generating the first plasma, the first gas is not supplied in the liquid, and
   the bubble contains a second gas.

2. The plasma generating method according to claim 1, wherein:
   hydrogen peroxide is generated in the liquid by the first plasma,
   the method further comprises:
   determining whether or not a concentration of the hydrogen peroxide in the liquid is a predetermined value or more, and
   in the second period, when the concentration is determined to be the predetermined value or more, the supplying the first gas is performed.

3. The plasma generating method according to claim 2, wherein the predetermined value is 10 ppm.

4. The plasma generating method according to claim 1, further comprising:
   after the first period and before the second period, stopping an application of the first voltage.

5. The plasma generating method according to claim 4, wherein:
   hydrogen peroxide is generated in the liquid by the first plasma,
   the method further comprises:
   after the stopping the application of the first voltage is performed, one of the outer walls is a bottom wall of the container.

6. The plasma generating method according to claim 1, wherein the first gas is at least one selected from the group consisting of air, nitrogen, and oxygen.

7. The plasma generating method according to claim 1, wherein, in generating the first plasma, no gas is supplied in the liquid.

* * * * *